United States Patent
Datt et al.

(10) Patent No.: US 10,561,701 B2
(45) Date of Patent: *Feb. 18, 2020

(54) MULTIFUNCTIONAL FORMULATION COMPRISED OF NATURAL INGREDIENTS AND METHOD OF PREPARATION/MANUFACTURING THEREOF

(71) Applicants: DATT MEDIPRODUCTS LIMITED, New Delhi (IN); DATT LIFE SCIENCE PVT. LTD., New Delhi (IN)

(72) Inventors: Rajan Datt, New Delhi (IN); Siddharth Pandey, New Delhi (IN); Pallavi Shrivastava, New Delhi (IN); Ramadhar Kumar, New Delhi (IN)

(73) Assignee: DATT LIFE SCIENCES PRIVATE LIMITED, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/115,695

(22) Filed: Aug. 29, 2018

(65) Prior Publication Data

US 2018/0369315 A1    Dec. 27, 2018

Related U.S. Application Data

(63) Continuation of application No. 15/384,383, filed on Dec. 20, 2016, now Pat. No. 10,076,552.

(30) Foreign Application Priority Data

Aug. 9, 2016  (IN) .............................. 201611027102

(51) Int. Cl.
*A61K 36/9066* (2006.01)
*A61K 36/886* (2006.01)
(Continued)

(52) U.S. Cl.
CPC .... *A61K 36/9066* (2013.01); *A61F 13/00012* (2013.01); *A61F 13/00017* (2013.01);
(Continued)

(58) Field of Classification Search
None
See application file for complete search history.

(56) References Cited

U.S. PATENT DOCUMENTS 5,466,542 A    11/1995  Kraetschmer et al.
5,648,380 A     7/1997  Martin
(Continued)

FOREIGN PATENT DOCUMENTS

WO    2007/103435    9/2007

OTHER PUBLICATIONS

Ganta et al., "Curcumin Enhances Oral Bioavailability and Anti-Tumor Therapeutic Efficacy of Paclitaxel Upon Administration in Nanoemulsion Formulation," Journal of Pharmaceutical Sciences, Published online in Wiley InterScience (www.interscience.wiley.com); Feb. 26, 2010; Wiley-Liss, Inc.; pp. 1-2.
(Continued)

*Primary Examiner* — Kyung S Chang
(74) *Attorney, Agent, or Firm* — Allen, Dyer, Doppelt & Gilchrist, P.A.

(57) ABSTRACT

This invention relates to a pharmaceutical preparation for the treatment of compromised tissue such as skin wounds and ulcers in humans and animals and a method of preparation. This is a multifunctional natural matrix meant for the treatment of compromised tissues which also relates to the anti-cancer transdermal patch for melanoma therapy. Further, the invention comprises for the treatment of Alzheimer's, and multiple sclerosis also. The composition consists of water-solubilized nano-sized formulation of non-aqueous solvent extract of phyto-pharmaceuticals in herbal, animal
(Continued)

or synthetic biocompatible gel or on matrix coated or both. The composition is used as a topical device for the treatment of compromised tissues in its preferred embodiment.

21 Claims, 8 Drawing Sheets

(51) Int. Cl.

| | |
|---|---|
| A61K 36/47 | (2006.01) |
| A61K 33/38 | (2006.01) |
| A61K 36/82 | (2006.01) |
| A61F 13/00 | (2006.01) |
| A61K 9/70 | (2006.01) |
| A61K 31/765 | (2006.01) |
| A61K 36/185 | (2006.01) |
| A61K 47/10 | (2017.01) |
| A61K 47/22 | (2006.01) |
| A61K 47/32 | (2006.01) |
| A61K 47/34 | (2017.01) |
| A61K 47/36 | (2006.01) |
| A61L 15/18 | (2006.01) |
| A61L 15/20 | (2006.01) |
| A61L 15/22 | (2006.01) |
| A61L 15/40 | (2006.01) |
| A61L 15/42 | (2006.01) |
| A61L 15/44 | (2006.01) |
| A61L 15/58 | (2006.01) |
| A61L 15/32 | (2006.01) |

(52) U.S. Cl.
CPC .......... *A61K 9/7069* (2013.01); *A61K 31/765* (2013.01); *A61K 33/38* (2013.01); *A61K 36/185* (2013.01); *A61K 36/47* (2013.01); *A61K 36/82* (2013.01); *A61K 36/886* (2013.01); *A61K 47/10* (2013.01); *A61K 47/22* (2013.01); *A61K 47/32* (2013.01); *A61K 47/34* (2013.01); *A61K 47/36* (2013.01); *A61L 15/18* (2013.01); *A61L 15/20* (2013.01); *A61L 15/225* (2013.01); *A61L 15/32* (2013.01); *A61L 15/40* (2013.01); *A61L 15/425* (2013.01); *A61L 15/44* (2013.01); *A61L 15/585* (2013.01); *A61F 2013/0091* (2013.01); *A61F 2013/00638* (2013.01); *A61F 2013/00646* (2013.01); *A61K 2236/33* (2013.01); *A61K 2236/51* (2013.01); *A61K 2236/53* (2013.01); *A61L 2300/104* (2013.01); *A61L 2300/30* (2013.01); *A61L 2300/404* (2013.01); *A61L 2300/62* (2013.01); *A61L 2300/802* (2013.01)

(56) References Cited

U.S. PATENT DOCUMENTS

| | | |
|---|---|---|
| 5,652,274 A | 7/1997 | Martin |
| 5,663,208 A | 9/1997 | Martin |
| 5,766,614 A | 6/1998 | Yong |
| 5,916,573 A | 6/1999 | Spiers et al. |
| 6,027,728 A | 2/2000 | Yuen |
| 6,063,402 A | 5/2000 | Gebert et al. |
| 6,126,950 A | 10/2000 | Bindra et al. |
| 6,133,440 A | 10/2000 | Qiu et al. |
| 6,183,761 B1 | 2/2001 | Bissett et al. |
| 8,759,403 B2 | 6/2014 | Chaniyilparampu et al. |
| 8,772,265 B2 | 7/2014 | Neven et al. |
| 8,785,380 B2 | 7/2014 | Madhavamenon et al. |
| 8,852,648 B2 | 10/2014 | Salamone et al. |
| 9,192,644 B2 | 11/2015 | Frautschy et al. |
| 9,259,401 B2 | 2/2016 | Deshpande et al. |
| 2003/0153512 A1 | 8/2003 | Hergenhahn et al. |
| 2007/0148263 A1 | 6/2007 | Antony |
| 2018/0042980 A1 | 2/2018 | Datt et al. |

OTHER PUBLICATIONS

Barik et al., "Curcumin Loaded Hydrogels as Probable Drug Delivery Systems," National Academy Science Letters 28(11):383-388; Jan. 2005; Abstract Only, 1 page.

Bisht et al., "Polymeric Nanoparticle-Encapsulated Curcumin ("Nanocurcumin"): A Novel Strategy for Human Cancer Therapy," Journal of Nanobiotechnology (5:3), Apr. 17, 2007; pp. 1-18.

MULTIFUNCTIONAL FORMULATION COMPRISED OF NATURAL INGREDIENTS AND METHOD OF PREPARATION/MANUFACTURING THEREOF

CROSS REFERENCE TO RELATED APPLICATION

This is a continuation application based on U.S. patent application Ser. No. 15/384,383 filed on Dec. 20, 2016, which application takes the benefit of and in turn claims priority under 35 USC § 119 to Indian Patent Application No. 201611027102 filed on Aug. 9, 2016, the contents of which are herein incorporated by reference.

FIELD OF THE INVENTION

The present invention relates to the field of medical biotechnology.

More particularly, the present invention relates to providing innovative product for wound healing.

The present invention provides novel products for use in the field of wound healing and anticancer formulation.

Even more particularly, the present invention relates to the field of wound healing dressing device and patches.

The present invention provides a wound healing matrix which comprises of a variety of natural ingredients, all working together in a synergistic way to achieve the desired results.

Further, the present invention provides novel products to be used in the field of anti-Alzheimer's and multiple sclerosis formulation.

BACKGROUND OF THE INVENTION

This invention relates to a formulation of composite phytopharmaceuticals containing gel prepared using natural gel like materials and or biocompatible medical grade silicon base coated on porous and breathable matrix of polyurethane or cotton to be used for the treatment of wounds and ulcers in humans and animals. It also relates to the formulation of transdermal patches for delivery of the phytopharmaceuticals. The invention comprises the properties of anti-inflammatory, anti-oxidant, anti-microbial, anti-cancer and wound healing potentials. Further, the invention also comprises useful for Alzheimer's and multiple sclerosis.

The use of wound dressings to cover and protect wounds is very well known. Preferably, the wound dressing should provide a sterile environment at the wound site and should rapidly absorb wound exudates while maintaining a moist wound surface. The dressing should interfere as little as possible with wound healing and should be easy to remove and replace with minimal trauma. Finally, the wound dressing should be inexpensive to make, compact and conformable to all skin surfaces.

The process of wound healing consists of three phases during which the injured tissue is repaired, regenerated, and new tissue is reorganized into a scar. The fibroblasts, endothelial cells, and epithelial cells migrate in the wound site. These fibroblasts produce the collagen that is necessary for wound repair. In re-epithelialization, epithelial cells migrate from the free edges of the tissue across the wound. This event is succeeded by the proliferation of epithelial cells at the periphery of the wound. Research has also shown that re-epithelialization is enhanced by the presence of occlusive wound dressings which maintain a moisture barrier.

A large variety of treatment and modalities are available for the treatment of wounds and ulcers as described here. These range from applications of antibiotics, occlusive layers, bandages, poultices, mechanical devices that reduce evaporation of water and many others. However, all of these modalities have one drawback in common; they all enhance wound healing by supporting the body mechanisms to heal the wound. Unfortunately, the passive healing process results in much disappointment because the body may have compromised immunity or other body functions that may not work optimally. What is needed is a modality of treatment that will actively regenerate the skin, dermis and epidermis. In the invention described here, the specific composition actively promotes healing by stimulating stem cells that are present even in deep wounds and burns to regenerate the lost tissue. Stem cells are by definition present in all self-renewing tissues. These cells are believed to be long-lived, have a great potential for cell division and are ultimately responsible for the homeostasis of steady-state tissues. Stem cells are normally slow cycling. They can, however, be induced to enter the proliferative pool in response to certain growth stimuli. A number of growth factors have been reported to be useful for modulating stem cell activity. For example, cytokines such as Tumor Necrosis Factor (TNF), Epidermal Growth Factor (EGF), Transforming Growth Factor (TGF) and Interleukin-1 (IL-1) are believed to be useful. Because stem cells are normally slow cycling but proliferate rapidly upon inductive stimulation, they may be attractive targets for cytokines.

Several herbal products have been proposed for the treatment of wounds and ulcers. U.S. Pat. No. 6,133,440 provides a rapid and efficient method for the preparation and isolation of biologically active polysaccharides from *Aloe*, "Immuno-10" and the use of the polysaccharides as immunostimulating, immunomodulating and wound healing agents. U.S. Pat. No. 6,027,728 comprises a selection of herbal materials with curative effects combined in a powdered form for application to human skin to accomplish skin regeneration, particularly for application to human skin affected with eczema, psoriasis, allergic reactions, inflammatory rash and the like. The process of application is critical to effectiveness of the present invention. The application of the herbal powder to the skin is intended to cause a temporary inflammation.

A variety of other herbal extracts may be included, and the compositions may take the form of a cream or ointment based on ghee, or they may be in a powdered form of suitable for preparing decoctions in hot water. U.S. Pat. No. 5,766,614 is a new burn treatment composition which provides healing to the skin of people who have received burns or are afflicted with other skin complications that require healing. U.S. Pat. No. 6,126,950 relates to a formulation of herbal cream for cracked heels and palms. It is comprised of a natural wax as an emulsifier, extract of *Curcuma* and the gum of *Acacia* or *Colophonium* or *Shorea*. The gum gives a synergistic effect in binding and healing the skin with natural wound healing herbal extract selected from the aqueous extracts of *Curcuma*, neem and allantonin.

The herbal gel formulation of the present invention consists of a natural herbal nono-aqueous extract of *Curcuma longa*, curcumin, non-aqueous extract of *Emblica officinalis* and *Camellia sinensis* and silicon and/or *Aloe vera* gel and or polymers viz. gelatin, collagen, carboxymethyl cellulose, alginate, polyvinyl alcohol, polyvinyl pyrrhilidon or equivalent. The healing property including anti-microbial, anti-inflammatory and anti-oxidant nature of curcumin is well established and gel of *Aloe vera* and silicon have been used which are also well known for wound management. The used other two extracts viz. *Emblica officinalis* and *Camellia sinensis* are also well known for anti-microbial, anti-oxidant and anti-inflammatory potentials including wound healing promoting agents. The synergistic action of *Curcuma longa* extract, curcumin, *Emblica officinalis* and *Camellia sinensis* along with *Aloe vera* gel and/or silicon quickens the healing, binds the skin and makes it soft and supple. A silicon based composition has been added which enhances the soothing and healing property along with *Aloe vera* and other composition used. Further, this formulation has been coated on porous and breathable matrix of polyurethane and/or cotton to make it a complete wound dressing solution. Furthermore, these nano-formulations are combined with transdermal patches for transdermal drug delivery devices preferably delivering anti-cancer drug.

The prior art relevant to this invention consists of various wound healing, antimicrobial, anti-oxidant and anti-inflammatory compositions comprised of one or a few of the above ingredients and other herbal and chemical mixtures. Further, it also has got anti-cancer potential.

It is known in the art that skin wound healing may be enhanced by the topical application of vitamin, herbal and/or chemical compositions to the affected area or through the ingestion of some such compositions. However, existing inventions inadequately address the need for a therapeutic composition that is all natural, provides fast pain relief, and acts as anti-microbial and anti-oxidants, reduces inflammation and enhances the healing of wounds and ulcers; and also acts as anti-cancer agents.

U.S. Pat. No. 5,466,542 is a pharmaceutical composition for the treatment of skin disorders comprised of extracts of herbs to provide an anti-inflammatory agent, an adrenocortical stimulant and a cortisol protecting agent. U.S. Pat. No. 5,648,380 is a therapeutic anti-inflammatory wound healing composition comprised of an anti-inflammatory agent and a wound healing composition. The wound healing composition is comprised of pyruvate, an antioxidant and a mixture of saturated and unsaturated fatty acids. The anti-inflammatory agent may be chosen from a group consisting of etodalc, Evening Primrose Oil, salsalate, cortisone and select others. The antioxidant may be chosen from a group consisting of all forms of Vitamin A, Vitamin C, Vitamin E and mixtures thereof. The composition is also comprised of a pharmaceutically acceptable carrier. U.S. Pat. No. 5,663,208 is an anti-fungal wound healing composition with anti-fungal agent comprised of lactic and sorbic acid, terconazole or select others. U.S. Pat. No. 5,652,274 by A. Martin, filed a therapeutic wound healing composition comprised of pryuvate, and antioxidant and a mixture of saturated and unsaturated fatty acids. U.S. Pat. No. 5,916,573 is a topical treatment of the skin, comprised of grape-seed oil, a hydrating agent that may be chosen from a group consisting of Vitamin E oil, Primrose oil and select others, an amino acid and deionized water. U.S. Pat. No. 6,183,761 by D. L. Bissett, filed Mar. 12, 1999, is a composition for regulating skin appearance comprised of a Vitamin B3 compound, a polycyclic compound, flavanones, chalcones, isoflavones, coumarins, chromones, dicomarols, chromanols, sterols, selected others and mixtures thereof. Further reference may be made to Ganta S, Devalapally H, Amiji M. curcumin enhances oral bioavailability and anti-tumor therapeutic efficacy of paclitaxel upon administration in nanoemulsion formulation. J pharm sci 2010; 99: 4630-41. Barik A, Praveen N, Indira Priyadarsini K, Kumar m, mohan h. curcumin loaded hydrogels as probable drug delivery systems. National academy science letters 2005; 28: 383-8. Bisht S, Feldmann G, Soni S, Ravi R, Karikar C, Maitra A, Maitra A. polymeric nanoparticle-encapsulated curcumin ("nanocurcumin"): a novel strategy for human cancer therapy. J nanobiotechnology 2007; 5:3. Curcumin derivatives with improved water solubility compared to curcumin and medicaments containing the same (US20030153512).

As disclosed above, a number of compositions exist, and are composed of herbs, chemicals, and vitamins. However, none of the inventions in prior art teach about a composition which uses the ingredients as provided in present invention and showing efficiency. Therefore, it is very important to provide solutions which can solve the above problems in innovative manner. The present invention provides such solution.

Further, none of the prior art discloses an invention that utilizes a topically administered natural therapeutic composition for the treatment of diseases and wounds comprised of a mixture of nano-curcumin, nano-*Emblica* and nano-*Camellia* extract contained in *Aloe vera* and/or silicon based gel. Further, the same is coated on porous and breathable matrix. Furthermore, same is formulated either in combination or individually as transdermal patch for transdermal drug delivery system for therapy of compromised tissues including cancer therapy. Further, the invention also comprises beneficial use for Alzheimer's and multiple sclerosis.

The invention described here comprises a mixture of four herbs and one synthetic polymer, silicon, which (three out of four herbs) are extracted by soaking in non-aqueous solvent e.g. more than 99% ethanol or different ratio of solvent e.g. 1:2.5 wt/wt of acetone:ethanol and formulated to make it water soluble towards enhancing bioavailability. Further, this formulation has been upgraded in terms of better efficacy by using biopolymeric sandwich model and/or synthetic polymer viz. silicon or both. Polymers may be synthetic of biopolymers. Biopolymers may contain from a source of protein e.g. collagen, gelatin or polyschaccharide e.g. chitosan carboxymethyl cellulose or both.

The phytopharmaceutical preparation of the invention described is meant to relieve pain, provides soothing effect and upon repeated use, has the ability to heal the wounds by providing a moist healing environment and stimulating stem cells to regenerate the lost tissues. The transdermal patch formulated with phytopharmaceutical preparation intended for transdermal delivery system preferably for cancer therapy either individually or combination.

In the present invention, water insoluble curcumin from *Curcuma longa*, extract of *Emblica officinalis* and *Camillia sinensis* have been subjected to physico-chemical treatment to solubilize in water and water soluble nano-sized formulation has been developed to enhance the bioavailability of the bioactive bio-molecules, had inherent water insolubility.

Curcumin is a water insoluble candidate isolated from *Curcuma longa*, its biological efficacies include anti-tumor, anti-inflammatory and anti-oxidant activities. In addition, curcumin displays therapeutic potential for neurological disorders such as Alzheimer's disease. A promising advantage of curcumin is that it displays minimal side effects in clinical applications as the drug. However, the practical applicability of curcumin is limited due to its low bioavailability which is due to poor aqueous solubility, poor gastrointestinal absorption, efficient first pass metabolism and rapid elimination. Therefore, an efficient drug delivery system is anticipated to be a breakthrough technology for the successful medical application of curcumin. Two main approaches are being employed to increase the bioavailability of curcumin. One strategy is based on the chemical modification of the curcumin molecule into water-soluble derivatives. Curcumin possesses two reactive terminal hydroxyl groups. These water-soluble curcumin derivatives might be patentable and considered as drug candidates. Another strategy is based on the nano-particulate drug delivery system. Many types of blend with nano-particles curcumin using polymers (e.g. PLGA) have been tested as drug delivery carriers. Several patents are lined up for curcumin formulation towards increasing its bioavailability includes US 20070148263, WO 2007103435, U.S. Pat. Nos. 6,063,402, 9,192,644, 9,259,401, 8,759,403, 8,772,265. These nano-particulate drug delivery systems appear to be a promising strategy for curcumin delivery. However, some other claim or report (U.S. Pat. No. 8,785,380) stated about dry curcumin powder suspended in excess water containing with or without hydrocolloids under ultrasound mediated ultrasonication, homogenization or cryogenic grinding and basis for carrier are required but none of them provided water soluble and nano form of curcumin and/or other water insoluble phytochemicals in the same form as like curcumin. In the present invention, using a simple physioco-chemical treatment, the water insoluble bioactive phytopharmaceuticals themselves were in nano sized form and water soluble without adding any polymers or surfactant or emulsifier or any equivalent factors reported as nano-formulators and hydrophilic carriers.

As stated above, similarly the non-aqueous extraction of the *Emblica officinalis* and *Camellia sinensis* and other plants or herbs was also water insoluble having potential bioactivities but less bioavailability. In the present invention, we adopted another approach i.e. physico-chemical treatment to make pure water insoluble curcumin and non-aqueous extract (water insoluble) of *Emblica officinalis* and *Camellia sinensis* into water soluble and nano-sized without using any polymeric carrier in terms of particulate or fiber or gel. The said physico-chemical treatment includes alteration of the pH at different interval of time and ultra-sonication. Following this, the water-solubilized extracts including curcumin were freeze-dried and further directly dissolved in pure water to get water soluble extract. The nano form of curcumin, phytochemical extract of *Emblica officinalis* and *Camellia sinensis* and other medicinal plants can also be obtained by high pressure homogenization followed by freeze-drying and further directly dissolved in pure water to get water soluble extract. Further, this approach has been extended and used to make water soluble to the other poor aqueous soluble or insoluble herbal extracts.

Further, it also provides the solution as anti-cancer, anti-Alzheimers and anti-multiple sclerosis in the form of transdermal patch and/or injectables.

SUMMARY OF THE INVENTION

The primary objective of the present invention is to provide a wound healing matrix and bandage.

Another objective of the invention is to provide a multi-purpose wound healing matrix with bandage.

Another objective of the invention is to provide a formulation with enhanced bioavailability of its ingredients.

Another objective of the invention is to provide a wound healing matrix which is made up of the natural ingredients.

Another objective of the invention is to provide a matrix/bandage which exhibits good antibiotic, anti-inflammatory and/or anti-oxidant properties and anti-cancer potentials.

Another objective of the invention is to provide a product which is also useful for Alzheimer's and multiple sclerosis.

Another objective of the invention is to provide a bandage in which all the components of the matrix work in a synergistic way to provide the desired healing results.

The present invention provides a formulation with enhanced bioavailability of its ingredients, working together in synergistic way. The said formulation of present invention is applied on a multi-purpose wound healing matrix with bandage.

The present invention relates to a naturalformulation and associated matrix bandage for compromised tissues viz. skin having wounds or melanoma. The formulation comprises of nano and water soluble formulation of water insoluble herbal extract to enhance their bioavailability.

The most important part is that natural water insoluble ingredients are used as part of formulation and their bioavailability is enhanced to great extent to make them effective, in much more range/amount than already known in prior art.

Since the components in the formulation are from herbal/naturalresources, it is very safe and eco-friendly and does not produce any adverse effect on the skin. The herbal gel formulation of the present invention consists of a natural herbal extract of *Curcuma longa, curcumin*, non-aqueous preferably ethanolic extract of *Emblica officinalis* and *Camellia sinensis* and silicon and/or *Aloe vera*. The gel can be used directly on to the compromised tissue or combined with a non-adherent carrier of breathable porous matrix of polyurethane or cotton gauze or equivalent. The active ingredients of the gel viz. nano-formulated water-solubilized agents/extracts e.g. water soluble pure nano-curcumin are also formulated as transdermal drug delivery patch for the delivery of herbal molecules for the treatment of cancer viz. melanoma. Further, the present invention also comprises beneficial use for Alzheimer's and multiple sclerosis.

Accordingly, the present invention provides a ready to use, flexible, multifunctional biocompatible bandage dressing and a method of manufacturing thereof, said dressing comprising a matrix based structure, having a plurality of biopolymers or synthetic polymers in the form of a formulation, with all ingredients working together in synergy, said matrix contained with the water soluble nano-form of non-aqueous solvent-extracted, water-insoluble phyto-pharmaceuticals from different natural sources, and a gel that is from herbal, animal or synthetic sources; such that the ingredients of formulation have much enhanced bioavailability than their naturally known values thus making it highly effective for wound healing, drug-delivery and anti-cancer therapy.

DETAILED DESCRIPTION OF THE SEVERAL EMBODIMENTS

Figure 1:
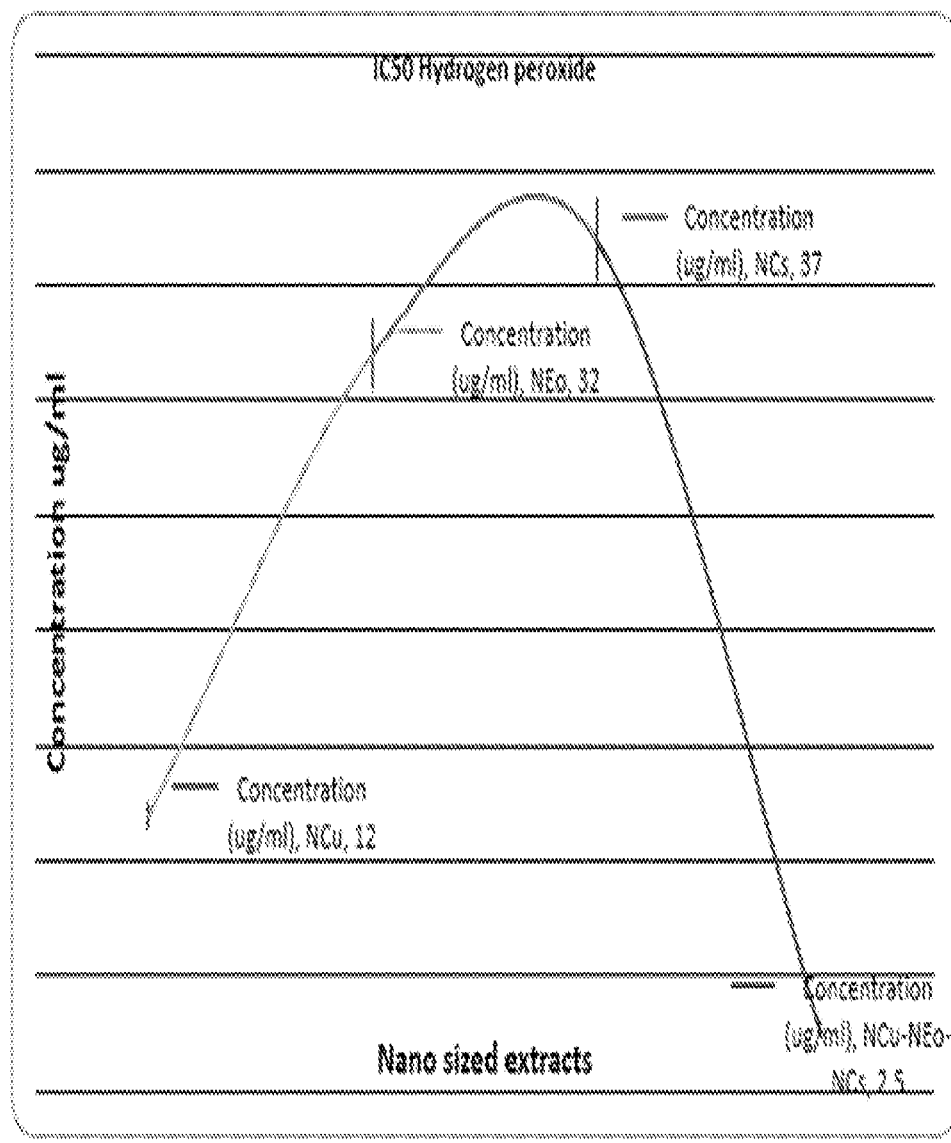
FIG. 1 illustrates a graph displaying in vitro anti-oxidant potential of physico-chemical treated nano-sized extracts.

It should be noted that the particular description and embodiments set forth in the specification below are merely exemplary of the wide variety and arrangement of instructions which can be employed with the present invention. The present invention may be embodied in other specific forms without departing from the spirit or essential characteristics thereof. All the features disclosed in this specification may be replaced by similar other or alternative features performing similar or same or equivalent purposes. Thus, unless expressly stated otherwise, they all are within the scope of present invention. Various modifications or substitutions are also possible without departing from the scope or spirit of the present invention. Therefore, it is to be understood that this specification has been described by way of the most preferred embodiments and for the purposes of illustration and not limitation.

The present invention provides a formulation with enhanced bioavailability of its ingredients, working together in synergistic way. The said formulation of present invention is applied on a multi-purpose wound healing matrix with bandage.

The present invention relates to a naturalformulation and associated matrix bandage for compromised tissues viz. skin having wounds or melanoma. The formulation comprises of nano and water soluble formulation of water insoluble herbal extract to enhance their bioavailability.

The most important part is that natural water insoluble ingredients are used as part of formulation and their bioavailability is enhanced to great extent to make them effective, in much more range/amount than already known in prior art.

Since the components in the formulation are from herbal/naturalresources, it is very safe and eco-friendly and does not produce any adverse effect on the skin. The herbal gel formulation of the present invention consists of a natural herbal extract of *Curcuma longa*, curcumin, non-aqueous preferably ethanolic extract of *Emblica officinalis* and *Camellia sinensis* and silicon and/or *Aloe vera*. The gel can be used directly on to the compromised tissue or combined with a non-adherent carrier of breathable porous matrix of polyurethane or cotton gauze or equivalent. The active ingredients of the gel viz. nano-formulated water solubilized agents/extracts e.g. water soluble pure nano-curcumin are also formulated as transdermal drug delivery patch for the delivery of herbal molecules for the treatment of cancer viz. melanoma. Further, the present invention also comprises beneficial use for Alzheimer's and multiple sclerosis.

The present invention provides a healing wound bed matrix containing characteristics of antibiotic, anti-oxidant, anti-inflammatory, anti-cancer and biocompatible within or on the surfaces of the wound. Further, the present invention is also beneficial for Alzheimer's and multiple sclerosis treatment.

The matrix bed is in the form of fabric or in the form of bandage or in the form of fiber bundles or mesh or in the form of gel or in the form of transdermal patch (e.g. silicon) or in the form of breathable film and porous matrix of polymer e.g. Polyurethane (PU). The base matrix could any one of the above mentioned which can be coated three dimensionally with bioactive nano-formulation of *Aloe vera* or silicone gel containing curcumin, *Emblica* and *Camellia* extract as a primary layer and which on one side is coated with layer by layer of the bioactive nano-formulation of *Aloe vera* or silicone gel containing curcumin, *Emblica* and *Camellia* extract having higher concentration. This multilayer differential coating forms a graduated barrier and release layer of the formulation. The nano-formulation can be layered coated either with individual bioactive extract or in different combination of four viz. *Curcuma* extract, Curcumin; *Emblica* and *Camellia*. The layered coating can also be done on alternate basis of the individual or in combinations of some or all. Further the same could be altered using silicon based gel formulation. The transdermal patch based on silicone base material can also be used to deliver the bioactive extract preferably *Curcuma* extract, Nano-Curcumin towards dealing with cancer therapy, preferably melanoma.

The invention thus provides a matrix with multifunctional wound healing and anti-cancer therapy. The natural components which are used in various compositions for medicinal values here are: *Curcuma* extract, curcumin, *Emblica* extract, *Camellia* extract, *Aloe vera* extract and/or *Aloe vera* gel or equivalent gel.

Other compositions like silicon based gel either alone or in combination with *Aloe* gel and or extracts of the four may also be used.

Other more composition like silicon based gel or patch either alone or in combination with *Aloe* gel and or extracts of the four preferably nano-curcumin alone or in combination with nano-extract of *Emblica* extract, *Camellia* extract may be used as anti-cancer patch preferably for melanoma.

The embodiments of the present invention provide the matrices exhibiting anti-microbial, anti-inflammatory, anti-oxidant and anti-cancer properties. The matrix is in the form of fabric or in the form of bandage or in the form of fiber or in the form of gel or in the form of transdermal patch having micro needles. Blend of cancer (preferably melanoma) healing matrix components of wound bed matrix with nano-curcumin, with or without its other constituents. Nano-Curcumin and other nano-extract are made by physico-chemical treatment of the aqueous insoluble extracted powder (preferably ethanol extract) followed by ultrasonic wave at least 25 KHz for 15 min-5 Hrs at ice temperature to obtain gradation of the particle size and mixed aqueous solution of the some of the extracts or all together at different ratio. A method to delivering curcumin nano-particles targeting melanoma is preferably via transdermal drug delivery approaches using silicon based transdermal patch having micro needles.

Accordingly, the present invention provides a ready to use, flexible, multifunctional biocompatible formulation and bandage dressing and a method of manufacturing thereof, said formulation and dressing comprising a matrix based structure, having a plurality of biopolymers or synthetic polymers in the form of a formulation, with all ingredients working together in synergy, said matrix contained with the water soluble nano-form of non-aqueous solvent-extracted, water-insoluble phyto-pharmaceuticals from different natural sources, and a gel that is from herbal, animal or synthetic sources; such that the ingredients of formulation have much enhanced bioavailability than their naturally known values thus making it highly effective for wound healing, drug-delivery, anti-cancer therapy, anti-Alzheimer's and anti-multiple sclerosis.

In an embodiment, said plurality of biopolymers are selected from but not limited to *Emblica officinalis, Acacia catechu, Azadirachta indica, Curcuma longa, Camellia sinsensis, Mimosa pudica, Ocimum sanctum, Phyllanthus emblica, Ricinus communis, Terminalia arjuna, Withania somnifera, Bacopa monnieri* etc, combined with a gel that can be natural source like alginate, *Aloe vera*, carboxy methyl cellulose, gelatin, pectin or synthetic polymers like silicon/siloxane/Dimethicone/methicone/siloxysilicate and their derivatives.

In another embodiment, said matrix bed is in the form of fabric or in the form of bandage or in the form of fiber bundles or mesh or in the form of gel or in the form of transdermal patch (e.g. silicon) or in the form of breathable film and porous matrix of polymer e.g. Polyurethane (PU).

In another embodiment, said base matrix is coated three dimensionally, preferably with bioactive nano-formulation of *Aloe vera* or silicone gel containing curcumin, *Emblica* and *Camellia* extract as a primary layer and which on one side is coated with layer by layer of the bioactive nano-formulation of *Aloe vera* or silicone gel containing curcumin, *Emblica* and *Camellia* extract having higher concentration, such that this multi-layer differential coating forms a graduated barrier and release layer of the formulation.

In yet another embodiment, said nano-formulation is layered coated either with individual bioactive extract or in different combination of four viz. *Curcuma* extract, Curcumin; *Emblica* and *Camellia*.

In another embodiment, said layered coating is also be done on alternate basis of the individual or in combinations of some or all or altered using silicon based gel formulation.

In yet another embodiment, said transdermal patch based on silicone base material is used to deliver the bioactive extracts preferably *Curcuma* extract, Nano-Curcumin towards dealing with cancer therapy, preferably melanoma.

In another embodiment, said system comprising of a ready to use, flexible, multifunctional biocompatible matrix based dressing contained with water-soluble nano-form of non-aqueous solvent extracted water insoluble phyto-pharmaceutical from different plant sources, and gel that can be from herbal, animal or synthetic sources, for the for effective wound healing, anti-cancer therapy and the manufacturing of the same thereof.

In another embodiment, said dressing is made using a suitable material, selected from either a medical grade polyurethane or equivalent polymer film or cotton in the form of woven or nonwoven gauze, foam or scaffold made from biopolymers, such that it allows air to flow through it making the dressing breathable.

In yet another embodiment, said dressing consists of a layer of coating over the matrix, said coating being gel like in nature and is incorporated with the formulation of phyto-pharmaceutical, extracted from different plant sources that promotes the wound healing and regeneration of skin, said formulation having all ingredients working together in synergy and having enhanced bioavailability of naturally water-insoluble ingredients.

In another embodiment, said formulation of the phytopharmaceutical comprises of water soluble extract that is prepared from two or more plant sources selected from but not limited to *Emblica officinalis, Acacia catechu, Azadirachta indica, Curcuma longa, Camellia sinsensis, Mimosa pudica, Ocimum sanctum, Phyllanthus emblica, Ricinus communis, Terminalia arjuna, Withania somnifera, Bacopa monnieri* etc, combined with a gel that can be natural source like alginate, *Aloe vera*, carboxy methyl cellulose, gelatin, pectin etc or can be synthetic polymers like silicon/siloxane/Dimethicone/methicone/siloxysilicate and their derivatives, polyvinyl alcohol, polyvinylpyrrolidone etc.

In another embodiment, said formulation of the phyto-pharmaceutical comprises of water soluble extract that can be obtained by mixing different non-aqueous extracts using non-aqueous solvent from plants preferably *Emblica officinalis*, in the range of 0.5%-20%, *Camellia sinsensis* in the range of 1%-20%, and making water soluble curcumin solution in the range of 0.1%-12% mixed with *Aloe vera* gel in the range of 0.2%-12% along with 0.5-9% tocoferol or all mixed together, accompanied with nano-silver or nano-silver mixed with *Aloe vera* accompanied with *Aloe-Vera* layer by layer.

In another embodiment, a layer by layer matrix formulation is done by preparing 0.3-2.5% *Aloe-Vera* solution in water followed by preparation of nano-crystaline silvel solution using 1-10% silver, 0.5-6 parts of 0.5-3% *Aloe vera* solution and 0.3-5 part of nano-silver solution and mixing the solution uniformly using stirrer at the speed of 800-1200 rpm for 10-40 mins and coating the non-adherent porous breathable matrix, preferably 3D coating, then drying the coated matrix at 25-175° C. in presence or absence of light and repeating this step 2-10 times preferably 2-3 times; preparing 2-6% *Aloe vera* solution in water and another solution of 2-10% *Aloe vera* in nano-silver solution prepared earlier; taking the dried coated gauze previously to give 10-500 μm thick coats of 2-10% *Aloe vera* in nano-silver solution on one side using the coating machine followed by coating with 10-500 μm 2-6% *Aloe vera* in water on the same or both sides and repeating the process 2-10 times with or without drying the matrix in between the coating steps; drying of the intermediate and the final coated matrix at 25-175° C. in presence or absence of light; optionally combining the steps used for nano-silver with nano-phyto-extracts in the 0.2-20 ratio of both preferably 1:4 ratio or optionally replacing the steps used for nano-silver, nano-silver with other nanoparticles of other metal and/or their derivatives viz gold, zinc, zinc oxide, copper, copper oxide, etc.; also optionally in steps used for nano-silver, replacing entirely the metallic nanoparticles by nano-phyto-extracts and coating alternatively alone or along with *Aloe vera* gel to obtain the desired final product.

In another embodiment, said non-aqueous solvent is preferably ethanol, methanol, hexane, toluene, chloroform, di-chloro-methane, methylene chloride, acetone, alone or in combination with other solvent in ratio of 1:1-0.1:5 wt/wt.

In another embodiment, different mix of water-solubilized nano-formulation of non-aqueous extract have a range of 0.2-15%. In yet another embodiment, water-solubilized nano-sized phyto-pharmaceutical is further formulated in nano-carrier for targeted delivery in the form of nano-particles, liposome, polymer nano-encapsulated, sized 0.3-500 nm, linker conjugated or ligand conjugated for sustained, controlled and targeted delivery meant for anti-cancer, anti-Alzheimer's and anti-multiple sclerosis.

In another embodiment, in nano-carrier for targeted delivery in the form of nanoparticle, liposome, polymer nano-encapsulated, sized 0.3-500 nm, where linker conjugated or ligand conjugated are relating to blood brain barrier Receptor, blood brain tumor brain receptor, angiogenesis Receptor; cell penetrating peptide-TAT peptide (AYGRKKRRQRRR), transferrin receptor, Nicotinic acetylcholine receptors (nAChRs), brain capillary endothelial cells receptors, integrin $\alpha v\beta 3$-cRGD, LVD peptide; NG2 proteoglycan-TH10 peptide TAASGVRSMH, EGFR receptor, COX-2 receptor, ER+, PR+ 17b-beta estradiol, Used to manage tumors that test positive for either estrogen or progesterone receptors, HER2+ anti-HER2 mAb, KRRQQKIRKYTMRR, triple positive, triple negative, folate receptor and other equivalent.

In another embodiment, encapsulated form of said phyto-pharmaceuticals is linker conjugated or ligand conjugated.

In another embodiment, said nano-sized nano-formulation is coated onto the stent to be a part of constituent to prepare drug eluting stent.

In another embodiment, the synthetic polymers like silicon/siloxane/Dimethicone/methicone/siloxysilicate and their derivatives may contain aqueous or non-aqueous solubilized silver nano-particles in the range of 0.1-11%.

In another embodiment, non-aqueous solubilized nano-silver preferably is in toluene and or hexane.

In another embodiment, in order to get pure nano-silver loaded silicon patch, preferably toluene solubilized nano-silver is mixed with soft skin silicon adhesive and kept for 5-25 min under flowing air preferably under vacuum at room temperature followed by curing at 60 to 90° C. for a time period of 10 min to overnight.

In another embodiment, the layering of each zone of the bioactive agents may be from 1 μm-500 μm.

In another embodiment, said matrix is of silicon based contains nano-phyto-extracts and/or nano-silver or both or alone as a silicon based patch may be or may not be with microneedles. The nano-phyto-extracts and nano-silver can be adsorbed, linked, conjugated or encapsulated with micro or nano-carriers.

In another embodiment, said matrix is of silicon based and contains nano-phyto-extracts and/or nano-silver or both or alone as a silicon based patch, manufactured by using 0.5-5% of nano-phyto-extracts, nano-curcumin or curcumin and nano-phyto-extracts; and coating the solution on a non-adherent surface preferably polyurethane film and then keeping it at 25-120° C. preferably at 80° C. from 30 mins to overnight.

In another embodiment, said formulation is accompanied by polymers like gelatin, collagen, chitosan, polyvinyl alcohol, polyvinyl pyrrhilidone, polyethylene glycol, mucopolysacchharides, carboxymethyl cellulose.

In another embodiment, the preferred ethanol extracts are prepared from the leaves of *Camellia sinsensis* and fruit of *Emblica officinalis*, in the following steps:
  adding dried and crushed plant to 100% non-aqueous solvent e.g. ethanol solution and keeping over magnetic stirrer for 20 hrs at 60° C.;
  separating the ethanolic extract by centrifugation at 8000 rpm for 15 mins;
  allowing the supernatant to dry in rotary evaporator or in oven at 30° C.-85° C.;
  preparing the solution of the desired concentration by dissolving the dried ethanolic extract in a 10%-20% ethanol solution and sonication at 5-85 amplitude for 15 min to 5 hrs followed by evaporation of excess of ethanol to form water soluble plant extract.

In another embodiment, said dressing is prepared by coating the phyto-pharmaceutical formulation over the woven cotton bandage followed by drying in air at room temperature in dark.

In yet another embodiment, said dressing is sterilized using gamma irradiation.

In another embodiment, said dressing is flexible and hence is used to cover the uneven surface of the compromised tissues of the body.

In another embodiment, said dressing is used for the wound management and is also used as transdermal drug delivery system preferably of silicon patch with micro needles towards the delivery of active phyto-pharmaceutical and their carrier for the treatment of the cancer preferably melanoma.

In another embodiment, said dressing possesses antimicrobial properties to prevent the growth of microorganism over the wounds thus accelerating the healing process.

In another embodiment, said dressing is capable of absorbing exudates from the wounds to provide favorable condition for the wound repair.

In another embodiment, said dressing can be used for various applications like exudating wounds in case of diabetic foot ulcers, venous ulcers or can be used for the covering the wound site created due to burns and also after surgical procedures.

In another embodiment, said dressing is preferably prepared in the form of a non-adherent gauze or patch.

The present invention is mainly for medical purpose and the broad range applications of the invention are as:
  Anti-microbial
  Anti-inflammatory
  Analgesic
  Antioxidant
  Wound healing
  Radiation poisoning
  Modulates immunity
  Biocompatible
  Haemostatic
  Non allergic
  Nano based technology for drug releasing
  Anti-cancer properties
  Multiple sclerosis
  Alzheimer's disease The following examples are for the purpose of illustration only and should not be construed to limit and the scope of the present invention.

EXAMPLE 1

Preparation of non-aqueous extract of *Emblica officinalis, Camellia sinensis* and *Curcuma longa* is performed preferably using 99.99% of ethanol followed by solvent evaporation to get water insoluble extract. The water insoluble extract was subjected to physico-chemical treatment by altering the pH of the solution followed by ultrasonic treatment at 5-25 amplitude for 2 to 5 hrs to get water soluble nano-sized fraction of non-aqueous (e.g. ethanolic) extracts. Yet another approach of curcumin, 1M solution of NaOH was prepared (pH of the solution was 12.5-12.6). 5-10% Curcumin solution was prepared in 1M solution of NaOH with continuous mixing. The prepared solution was then neutralized with 5N HCl and then adjusted to pH 5.5 The prepared solution was then sonicated for 5 hrs with amplitude and temperature maintained below 30° C. The obtained nano-formulation was assayed for anti-microbial, anti-inflammatory, anti-oxidant and/or anti-cancer potentials.

EXAMPLE 2

The obtained nano-formulation in example one is/are further subjected for formulation using silicon/siloxane/

Dimethicone/methicone/siloxysilicate based materials such as Dow Corning silicone elastomeric blend and soft skin adhesive etc from Dow Corning. The mixed subjects are kept for curing at temperature ranging from 10-150° C. to get gelly matrix, tacky less and tacky patches. The said nano-formulation could be loaded either individually or in combination onto the silicon based patches with micro needles meant for transdermal drug delivery. Individuality of the said nano-formulation such as water soluble pure curcumin could be loaded onto the micro needles containing silicon patch as a transdermal patch for melanoma therapy. Above obtained gel formulation may also contain tocoferol, vit E and glycerol.

EXAMPLE 3

The obtained nano-formulation in example one is/are coated onto the fabric preferably non-adherent fabric or polyurethane (PU) film or foam or breathable matrix. In a formulation of dressing matrix, nano-formulation of the three extract of *Emblica officinalis, Camellia sinensis* and *Curcuma longa* in the ratio of 1:1:1 at 5-15% concentration is coated on the pre-coated of silicon and/or *Aloe vera* gel fabric or PU film or foam or breathable matrix and dried at 4-25° C. followed by multiple coating-drying cycle layer by layer (L-B-L) to get different gradation of the bioactive agents. The layering thickness of each layered zone can be from 1 μm-500 μm. Multi-layered gradation of nano-formulated bioactive agents could be in different form such as (F1) Curcumin-*Emblica Officinalis-Camellia sinensis* (F2) *Camellia sinensis-Emblica officinalis*-Curcumin (F3) *Emblica officinalis*-Vit E-*Camellia sinensis*-Curcumin (F4) *Camellia sinensis-Aloe vera-Emblica Officinalis-Aloe vera*-Curcumin-*Aloe vera* (F5) *Camellia sinensis*-silicon-*Emblica Officinalis-Aloe vera*-Vit E-Curcumin and so on.

EXAMPLE 4

Take 10-50 ml of Dow corning soft skin adhesive and add 2-9 ml of Curcumin nano-particles dissolved in Dow corning SPE solution 2011 and mixed uniformly, and then make complete mixture with using the complete blend of soft skin adhesive. Cast the solution on to PU film and keep in air circulating oven at 80° C. for 10 mins. In another approach, keep in oven at 80° C. for 30 mins and 100° C. In yet another approach, curcumin nano-particles may be replaced or combined with silver nano-particles. To get only nano-silver loaded silicon patch, toluene solubilized nano-silver is mixed with Dow corning soft skin adhesive and kept for 5-25 min under flowing air or under vacuum at room temperature followed by curing at 80° C. for 10 min to overnight.

EXAMPLE 5

Take 20 ml of 5% curcumin nano-particle solution add 5 ml of 5% *Camellia sinsensis* extract in water, and then add 5% of *Emblica officinalis* extract in water, into it. Mix the complete solution by sonicating the extract blend as stated in example 1. Coat the blend over the woven cotton gauze (coated with non-adherent solution) using the coating machine. Allow the coated gauze to dry in air at 25° C. In another approach, take 50 ml curcumin nano-particles solution and use the solution for coating the pre-coated gauze using the coating machine. Allow the coated gauze to dry in air at 25° C. Prior coating, all the nano-sized extracts were in 0.5% of *Aloe vera* reconstituted gel.

EXAMPLE 6

Take 15 ml of 7.5% polyvinyl alcohol solution and then add 12 ml of 10% gelatin solution followed by adding 1 ml each of 2% chitosan solution, PEG 200 and glycerol. Mix the solution to prepare a homogenous blend to which adds 5 ml each of Dow corning soft skin adhesive complete pack. Mix the solution to form a homogenous mixture and then cast the blend on to the PU films and allow it to dry in air or oven at 60° C. In another formulation, take 15 ml of 7.5% polyvinyl alcohol solution and then add 12 ml of 10% gelatin solution followed by adding 1 ml each of 2% chitosan solution, PEG 400 and glycerol. Mix the solution to prepare a homogenous blend to which add 5 ml each of Dow corning skin adhesive and mix the solution to form a homogenous mixture and to which add 2 ml of Curcumin nano-particles dissolved in Dow corning SPE solution 2011, mix them properly, and then cast the blend on to the PU films or non-adherent gauze and allow it to dry in air or oven at 60° C. In yet another formulation, take 15 ml of 7.5% polyvinyl alcohol solution and then add 12 ml of 10% gelatin solution followed by adding 1 ml each of 2% chitosan solution, PEG 200 and glycerol. Mix the solution to prepare a homogenous blend to which adds 5 ml each of Dow corning skin adhesive. Mix the solution to form a homogenous mixture and to which add 2 ml of silver nano-particles with or without nano-curcumin, mix them properly, and then cast the blend on to the PU films and allow it to dry in air or oven at 60° C.

EXAMPLE 7

Prepare 0.5% P15 solution in USP grade water followed by reparation of nano-crystaline silvel solution using 1-10% silver.

Now take 3 parts of 0.5-3% *Aloe vera* solution and 1 part of nano-silver solution and mix the solution uniformly using stirrer at the speed of 800-1000 rpm for 10-20 mins and coat the non-adherent coated smart gauze and or another matrix mentioned before. The obtained coated matrix is dried at 25-175° C. avoiding exposure to the light while drying and this step is repeated. Now prepare 2-6% *Aloe vera* solution in water and another solution of 2-10% *Aloe vera* in nano-silver solution prepared earlier.

Take the dried coated gauze previously to give 10-100μ thick coats of 2-10% *Aloe vera* in nano-silver solution on one side using the coating machine followed by coating with 10-100μ 2-6% *Aloe vera* in water on the same side using the coating machine and repeat the process with or without drying the matrix in between the coating steps. Drying of the intermediate and the final coated matrix takes place at 25-175° C. avoiding exposure to the light while drying. The obtained products were tested on mice for their wound healing potentials comparing with existing dressing in market of the class.

Discussion of the Experiments Performed

The prepared multifunctional nano-formulation have efficacy like anti-microbial, biocompatible, anti-oxidant and anti-inflammatory and anti-cancer. Various experiments were conducted to check the said efficacy of matrix. Anti-microbial activities were studies using following bacteria and fungi viz. *Bacillus subtilis, Escherichia coli, Pseudomonas aeruginosa, Staphylococcus aureus* (including MRSA), *Candida albicans, Aspergillus niger.*

The biocompatibility, anti-oxidant and anti-inflammatory property of the said matrix were evaluated using mouse L929 fibroblastic cell line and human dermal fibroblasts viability, $H_2O_2$, DPPH (2,2-diphenyl-1-picrylhydrazyl) inhibition and Cox, Lox inhibition assay, respectively. The anti-cancer efficacy was tested using MCF-7, KB, INT-407, HCT-15, Colo-205, A-431, Hela cell line and the toxicity were compare using human normal primary fibroblast (HNPF).

Figure 2:
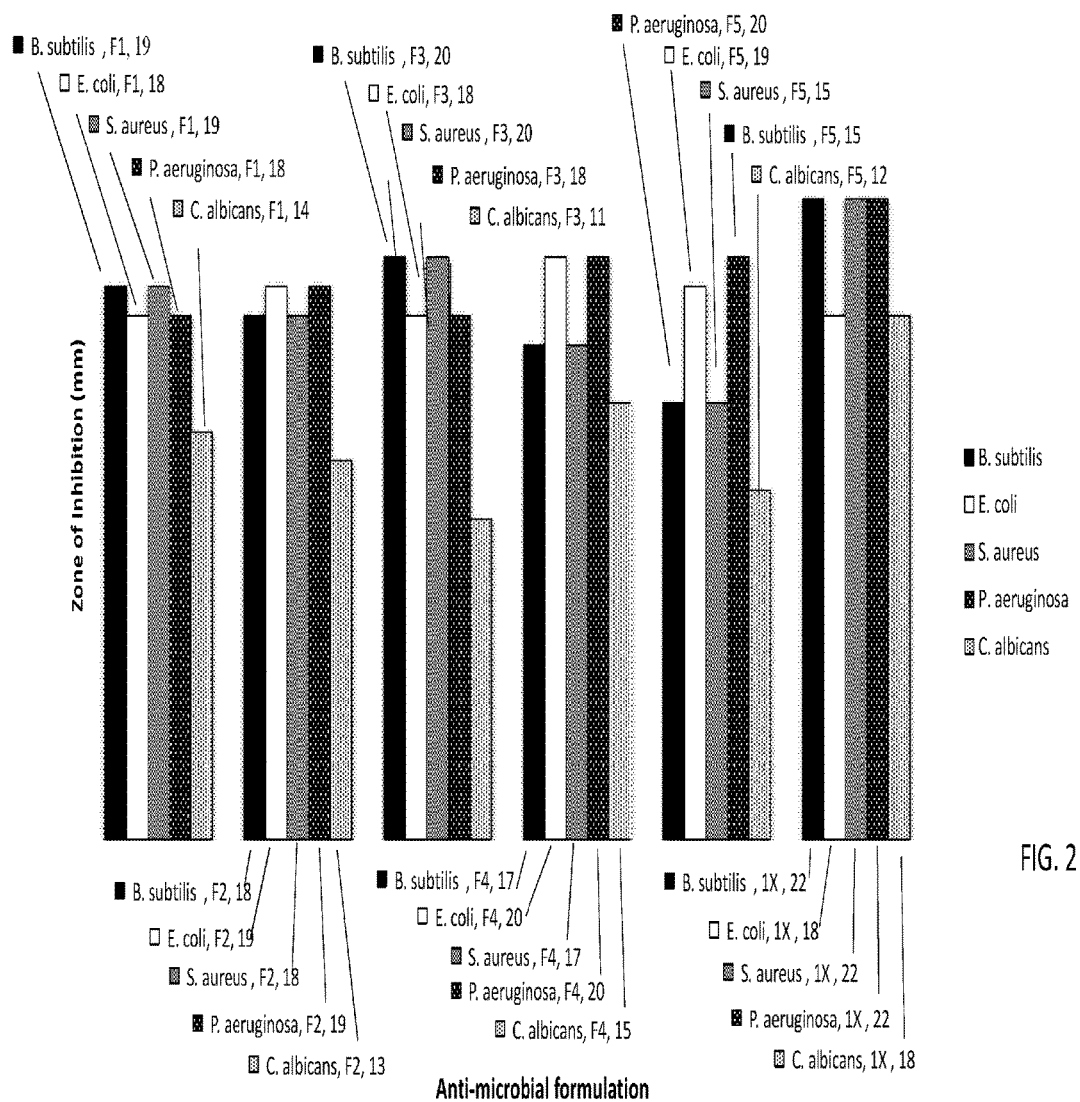
FIG. 2 illustrates a bar graph of mean zone of inhibition of *E. coli, S. bacillus, Staphylococcus aureus, Pseudomonas aeruginosa Candida albicans* using formulation F1-F5 and 1× antimicrobial solution at 24 Hrs.
Figure 3:
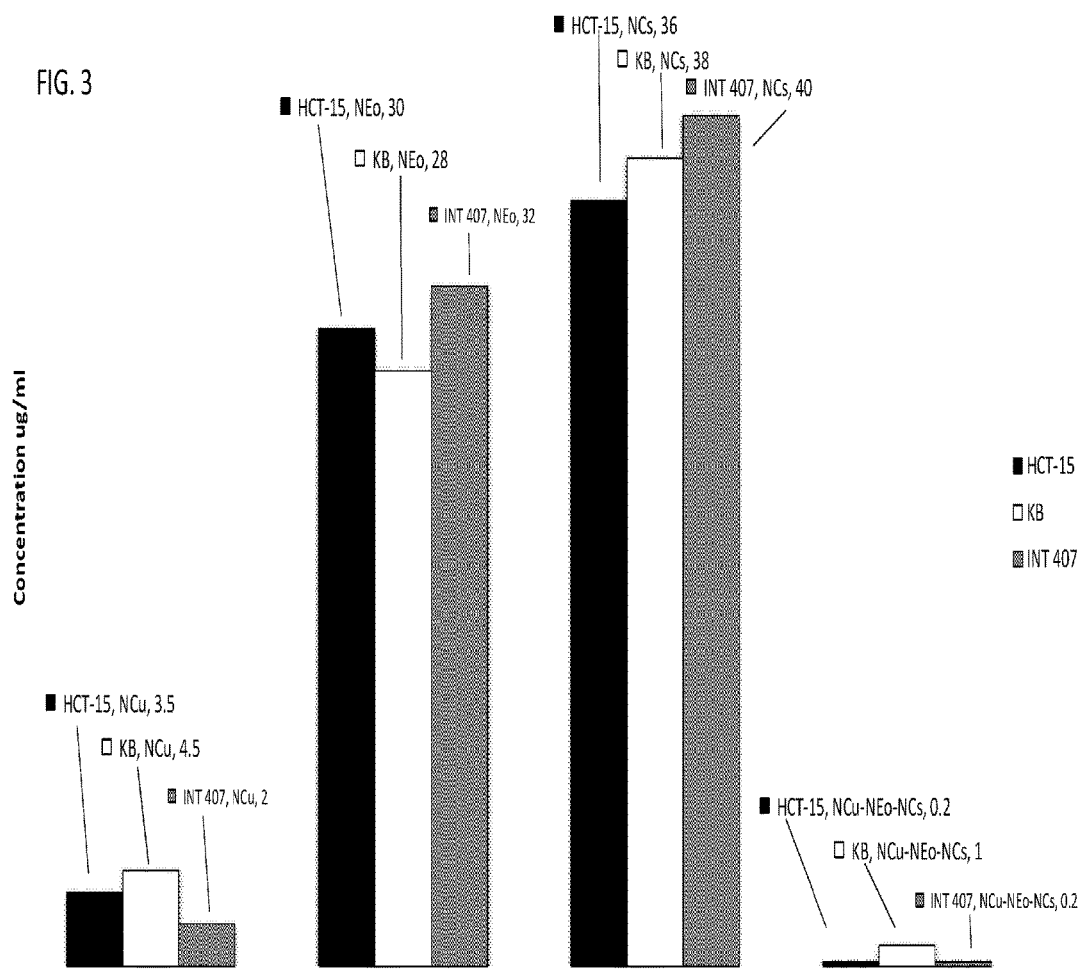
FIG. 3 illustrates a bar graph of the LD50 average of the nano-sized water solubilized curcumin extracts on HCT-15, KB and INT-407 cancer cell lines was found up to be 4.5 µg/ml.

The obtained results of anti-oxidant potential of the nano-sized extract contained formulation were considerably efficacious. The in-vitro anti-oxidant potential of some of the nano-sized extract and formulation are shown in FIG. 1. Similarly, anti-microbial activity, anti-inflammatory and anti-cancer potential were also considerably efficacious and the data for some of them are shown in this patent. Aqueous solution of nano-formulation of all three phyto-extracts in different combination at below 5% base concentration also resulted into 99.999% reduction in microbial CFU/ml in all time frames 30, 60, 90 and 120 seconds using time kill method. FIG. 2 is showing the anti-microbial potential of the formulation (F1-F5). FIG. 3 is showing the killing concentration of the water soluble nano-sized extracts. LD50 average of nano-curcumin on all used cancer cell lines was found up to be 4.5 µg/ml, which classifies the same as anti-cancer agent at very low concentration. Further, the combined formulation using nano-sized water soluble extract was found to have LD50 at concentration less than 1 µg/ml and it goes even beyond 0.2 µg/ml depending on cell types (FIG. 3). Further, dose toxicity on HNPF was very low even at very high dosage more than 30 µg/ml the novel nano-phyto-solution were non-toxic to HNPF which shows LD50 potential against the cancer cell lines while keeping normal cell almost unaffected. Anti-cancer property on some of the used cancer cell lines are shown in FIG. 3.

FIG. 1: In vitro anti-oxidant potential of physico-chemical treated nano-sized extracts. Data shows the IC50 value of the extract i.e. concentration at which $H_2O_2$ is inhibited by 50%. NCu: —Nano-sized curcumin; NEo: —nano-sized extract of *Emblica officinalis*; NCs: —nano-sized extract of *Camellia sinensis*; NCu-NEo-NCs:—1:1:1 ratio of NCu, NEo and NCs.

FIG. 2: Mean zone of inhibition of *E. coli, S. bacillus, Staphylococcus aureus, Pseudomonas aeruginosa Candida albicans* using formulation F1-F5 and 1× antimicrobial solution at 24 Hrs. F1: Curcumin-*Emblica officinalis*-*Camellia sinensis*; F2: *Camellia sinensis*-*Emblica officinalis*-Curcumin; F3: *Emblica officinalis*-Vit E-*Camellia sinensis*-Curcumin; F4: *Camellia sinensis*-*Aloe vera*-*Emblica officinalis*-*Aloe vera*-Curcumin-*Aloe vera*; F5: *Camellia sinensis* silicon-*Emblica officinalis*-*Aloe vera*-Vit E-Curcumin; 1×: 1× antimicrobial solution.

FIG. 3: The LD50 average of the nano-sized water solubilized curcumin extracts on HCT-15, KB and INT-407 cancer cell lines was found up to be 4.5 µg/ml. A combined formulation using nano-sized water soluble extract was found to have LD50 at concentration less than 1 µg/ml. NCu: —Nano-sized curcumin; NEo:—nano-sized extract of *Emblica officinalis*; NCs: —nano-sized extract of *Camellia sinensis*; NCu-NEo-NCs: —1:1:1 ratio of NCu, NEo and NCs.

The sizes obtained from the physico-chemical treatment of the extract were below 500 nm as shown in the scanning electron microscopic images 1, 2 and 3. And the LD50 of the nano-curcumin on HCT-15 was found to be 3.5 µg/ml. The morphology and concentration dependent killing of the HCT-15 cell lines are shown in the image 4&5 and FIG. 3 respectively.

The wound healing experimentation on mice were significantly efficacious in terms of epithilialization, wound contraction, and management of inflammation and pain comparing to other groups of mice used existing dressing of the same class.

Figure 4:
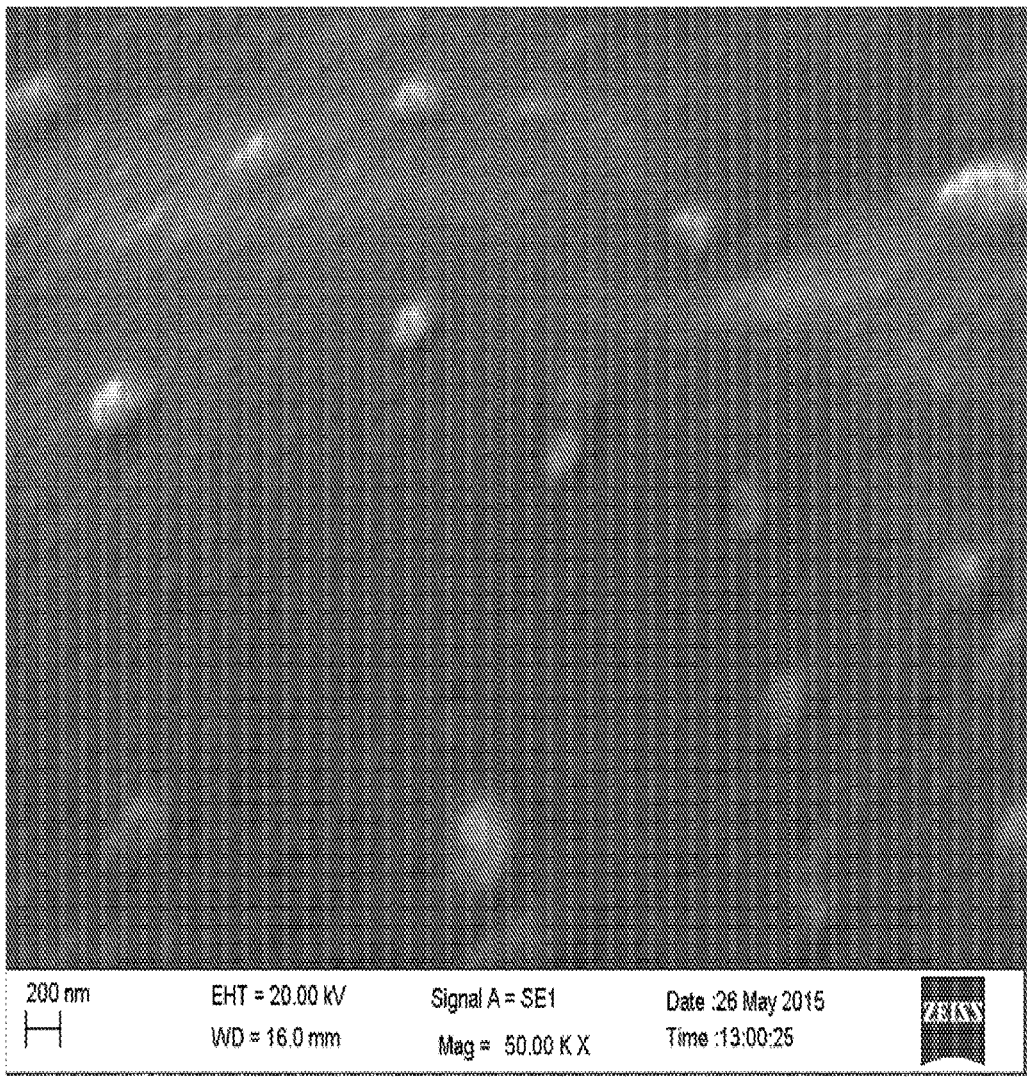
FIG. 4 illustrates a scanning electron microscopic image of water soluble nano-curcumin prepared by physico-chemical treatment.

FIG. 4: Scanning electron microscopic image of water soluble nano-curcumin prepared by physico-chemical treatment.

Figure 5:
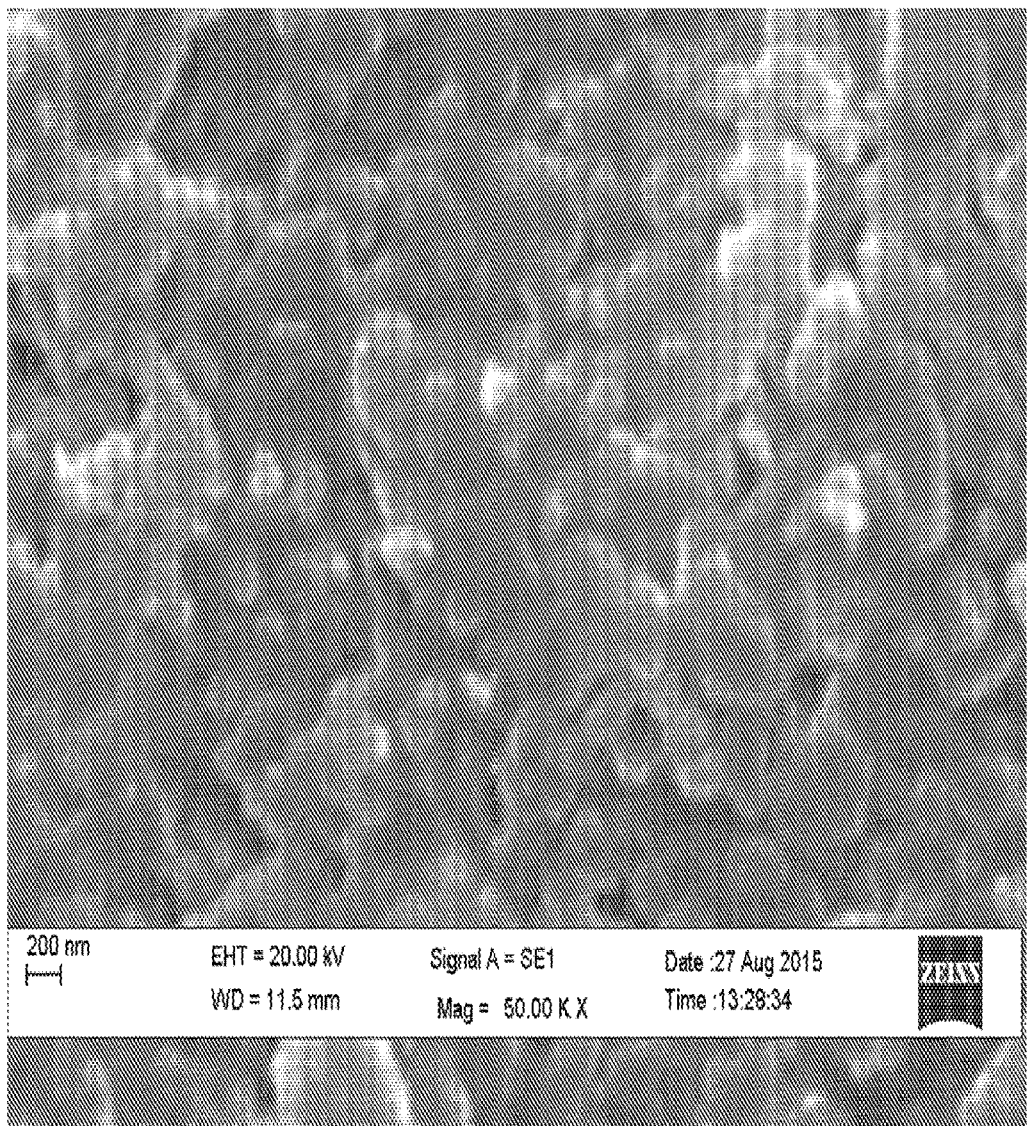
FIG. 5 illustrates a scanning electron microscopic image of water soluble nano-extract of *Emblica officinalis* prepared by physico-chemical treatment.

FIG. 5: Scanning electron microscopic image of water soluble nano-extract of *Emblica officinalis* prepared by physico-chemical treatment.

Figure 6:
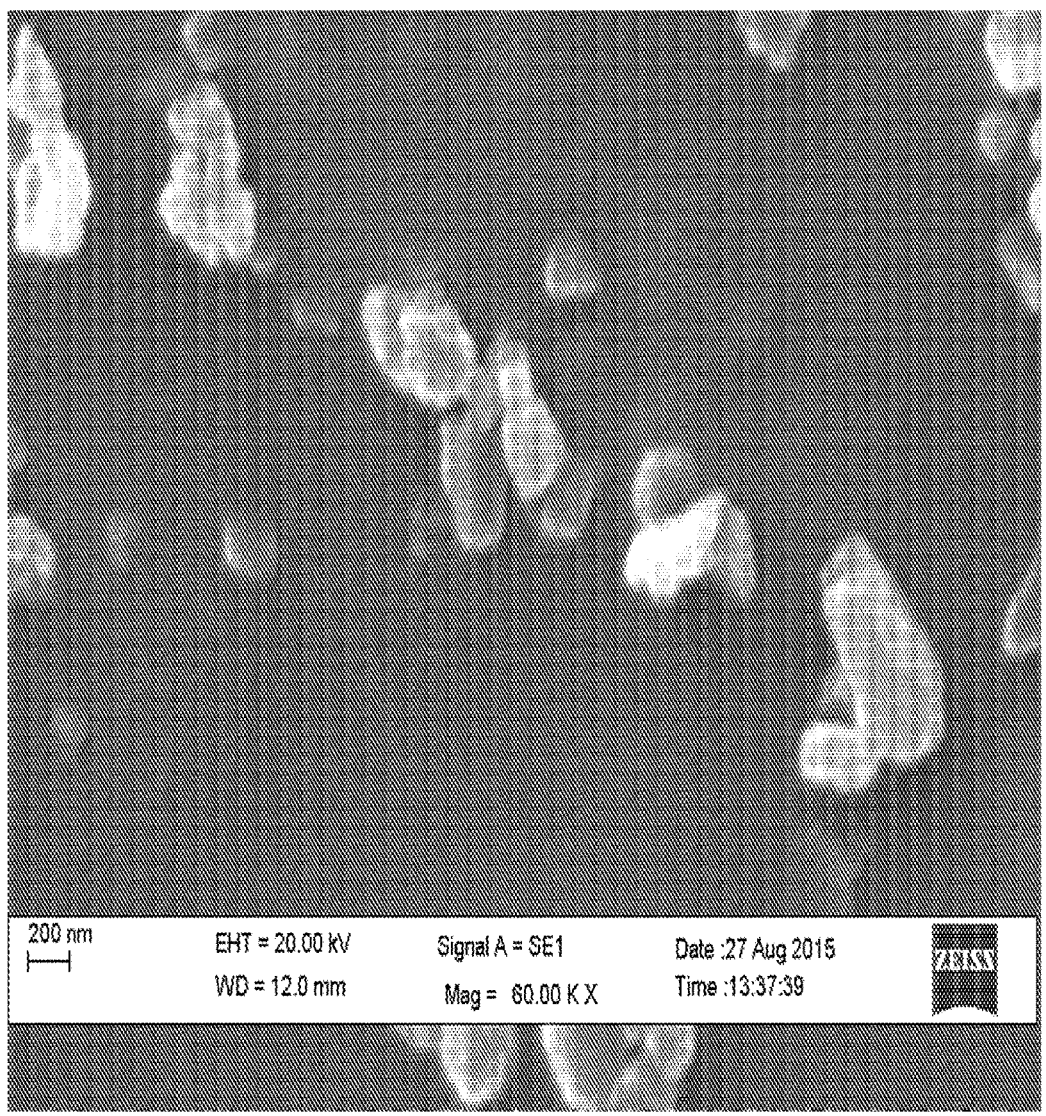
FIG. 6 illustrates a scanning electron microscopic image of water soluble nano-extract of *Camellia sinensis* prepared by physico-chemical treatment.

FIG. 6: Scanning electron microscopic image of water soluble nano-extract of *Camellia sinensis* prepared by physico-chemical treatment.

Figure 7:
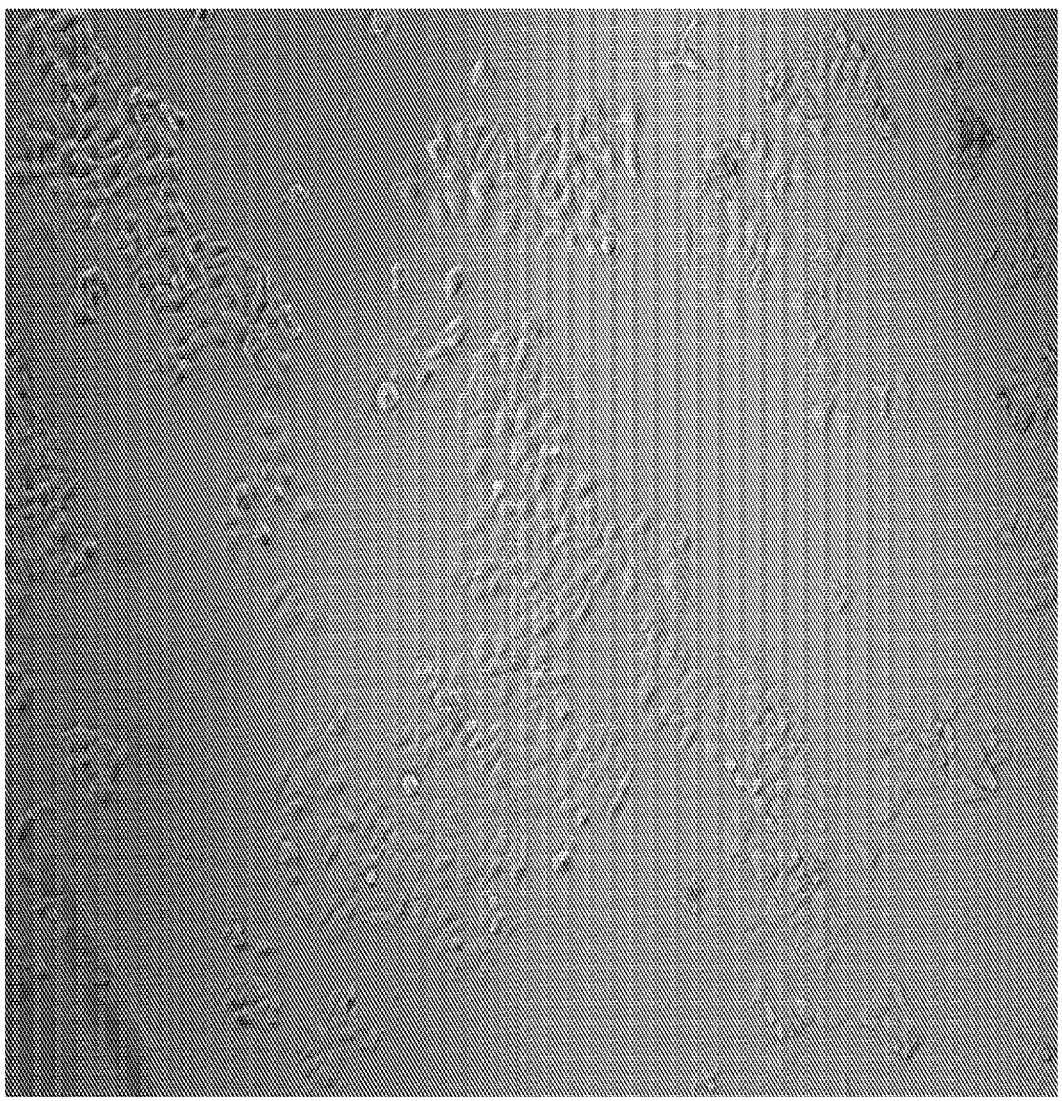
FIG. 7 illustrates a light microscopic image of HCT-15 cell line at 24 Hrs without treatment with water soluble nano-curcumin prepared by physico-chemical treatment.

FIG. 7: Light microscopic image of HCT-15 cell line at 24 Hrs without treatment with water soluble nano-curcumin prepared by physico-chemical treatment.

Figure 8:
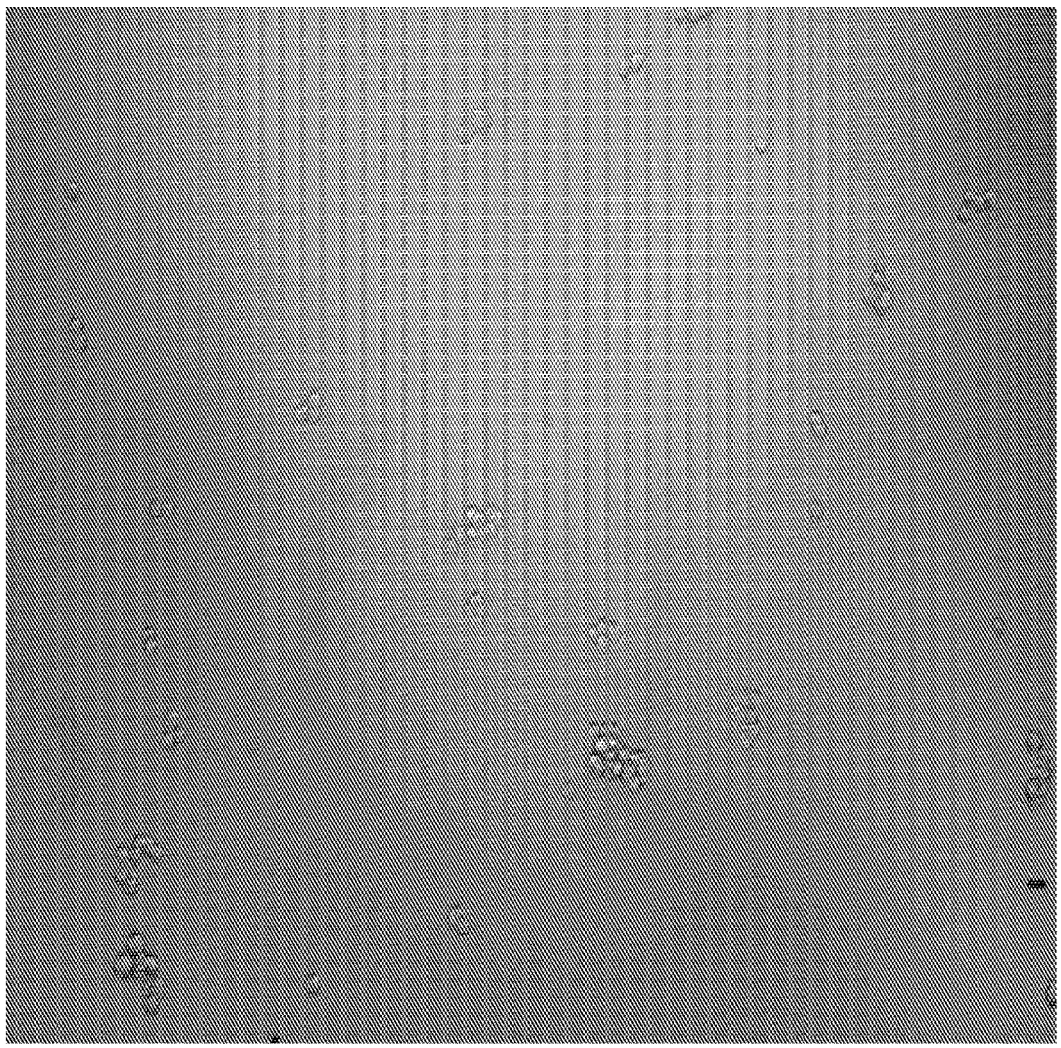
FIG. 8 illustrates a light microscopic image of HCT-15 cell line at 24 Hrs with treatment with 3.5 µg/ml of water soluble nano-curcumin prepared by physico-chemical treatment.

FIG. 8: Light microscopic image of HCT-15 cell line at 24 Hrs with treatment with 3.5 µg/ml of water soluble nano-curcumin prepared by physico-chemical treatment.

The obtained results of the potential and properties of the product of this invention were found considerably efficacious.

This product has resulted into 99.999% reduction in microbial CFU/ml in all time frames 30, 60, 90 and 120 seconds using time kill method.

This clearly indicates the technical advancement as compared to prior art.

What is claimed is:

1. A method of making a flexible, biocompatible bandage dressing comprising:
   preparing a phytopharmaceutical formulation by preparing a phytoextract solution containing 0.5 to 20 percent of non-aqueous extract from the plant *Emblica officinalis*, 1.0 to 20 percent of non-aqueous extract from the plant *Camellia sinsensis* and 0.1 to 12 percent of water soluble curcumin solution and mixing the phytoextract solution with 0.2 to 12.0 percent of *Aloe vera* gel;
   mixing the phytopharmaceutical formulation uniformly;
   applying a layer of the phytopharmaceutical formulation a plurality of times onto a biocompatible, porous matrix to form a coating that is between about 10 µm to 500 µm of the phytopharmaceutical formulation on the biocompatible, porous matrix; and
   drying the coating of the phytopharmaceutical formulation at 25 to 175 degrees C.

2. The method of claim 1, further comprising drying each layer of the phytopharmaceutical formulation at 25 to 175 degrees C. after each layer is applied.

3. The method of claim 1, further comprising mixing 0.5 to 9.0 percent tocopherol with the *Aloe vera* gel before mixing the *Aloe vera* gel with the phytoextract solution.

4. The method of claim 1, wherein the phytoextract solution is prepared from the leaves of *Camellia sinsensis* and fruit of *Emblica officinalis*, comprising the steps of:
   adding dried and crushed plants of the leaves of *Camellia sinsensis* and fruit of *Emblica officinalis* to 100% ethanol solution and stirring for about 20 hours at about 60 degrees C. to obtain an ethanolic extract;
   separating the ethanolic extract by centrifugation at about 8000 rpm for about 15 minutes to obtain a supernatant;
   allowing the supernatant to dry from about 30 degrees C. to about 85 degrees C. to obtain dried ethanolic extract; and preparing the phytoextract solution of desired concentration by dissolving the dried ethanolic extract in a 10%-20% ethanol solution and sonication at 5-85 amplitude for about 15 minutes to 5 hours followed by evaporating the excess ethanol to form a water soluble plant extract.

5. The method of claim 1, wherein the biocompatible, porous matrix comprises a woven cotton bandage.

6. The method of claim 5, wherein the drying of the coating of the phytopharmaceutical formulation occurs at 25 degrees C.

7. The method of claim 1, wherein the biocompatible, porous matrix comprises a silicon patch.

8. The method of claim 1, further comprising encapsulating the phytopharmaceutical formulation as liposomes having a diameter of about 0.3 to 500 nanometers.

9. The method of claim 1, further comprising applying a layer of the phytopharmaceutical formulation 2 to 10 times to form the coating that is between about 10 μm to 500 μm of phytopharmaceutical formulation on the biocompatible, porous matrix.

10. The method of claim 1, further comprising sterilizing the coating of the phytopharmaceutical formulation after drying by gamma irradiation.

11. The method of claim 1, wherein the *Aloe vera* gel is prepared from a 0.5 to 3.0 percent *Aloe vera* solution and 1.0 to 10.0 percent nano-silver solution.

12. The method of claim 1, wherein the phytopharmaceutical formulation is mixed uniformly with a stirrer at a speed of 800 to 1200 rpm for about 10 to 40 minutes.

13. A method of making a flexible, biocompatible bandage dressing comprising:
preparing a phytopharmaceutical formulation by preparing a phytoextract solution containing 0.5 to 20 percent of non-aqueous extract from the plant *Emblica officinalis*, 1.0 to 20 percent of non-aqueous extract from the plant *Camellia sinsensis* and 0.1 to 12 percent of water soluble curcumin solution and mixing the phytoextract solution with 0.2 to 12.0 percent of *Aloe vera* gel;
mixing the phytopharmaceutical formulation uniformly;
applying a layer of the phytopharmaceutical formulation a plurality of times onto a biocompatible, porous matrix formed as a silicon patch having microneedles for transdermal drug delivery to form a coating that is between about 10 μm to 500 μm of the phytopharmaceutical formulation on the silicon patch and microneedles; and
drying the coating of the phytopharmaceutical formulation at 25 to 175 degrees C.

14. The method of claim 13, further comprising drying each layer of the phytopharmaceutical formulation at 25 to 175 degrees C. after each layer is applied.

15. The method of claim 13, further comprising mixing 0.5 to 9.0 percent tocopherol with the *Aloe vera* gel before mixing the *Aloe vera* gel with the phytoextract solution.

16. The method of claim 13, wherein the phytoextract solution is prepared from the leaves of *Camellia sinsensis* and fruit of *Emblica officinalis*, comprising the steps of:
adding dried and crushed plants of the leaves of *Camellia sinsensis* and fruit of *Emblica officinalis* to 100% ethanol solution and stirring for about 20 hours at about 60 degrees C. to obtain an ethanolic extract;
separating the ethanolic extract by centrifugation at about 8000 rpm for about 15 minutes to obtain a supernatant;
allowing the supernatant to dry from about 30 degrees C. to about 85 degrees C. to obtain dried ethanolic extract; and
preparing the phytoextract solution of desired concentration by dissolving the dried ethanolic extract in a 10%-20% ethanol solution and sonication at 5-85 amplitude for about 15 minutes to 5 hours followed by evaporating the excess ethanol to form a water soluble plant extract.

17. The method of claim 13, further comprising encapsulating the phytopharmaceutical formulation as liposomes having a diameter of about 0.3 to 500 nanometers.

18. The method of claim 13, further comprising applying a layer of the phytopharmaceutical formulation 2 to 10 times to form the coating of the phytopharmaceutical formulation on the silicon patch and microneedles that is between about 10 μm to 500 μm thick.

19. The method of claim 13, further comprising sterilizing the coating of the phytopharmaceutical formulation after drying by gamma irradiation.

20. The method of claim 13, wherein the *Aloe vera* gel is prepared from a 0.5 to 3.0 percent *Aloe vera* solution and 1.0 to 10.0 percent nano-silver solution.

21. The method of claim 13, wherein the phytopharmaceutical formulation is mixed uniformly with a stirrer at a speed of 800 to 1200 rpm for about 10 to 40 minutes.

* * * * *